United States Patent [19]

Jhingan

[11] Patent Number: 5,204,246
[45] Date of Patent: Apr. 20, 1993

[54] DNA ISOLATION METHOD

[75] Inventor: Anil K. Jhingan, Polk County, Iowa

[73] Assignee: Pioneer Hi-Bred International, Inc., Des Moines, Iowa

[21] Appl. No.: 634,256

[22] Filed: Dec. 26, 1990

[51] Int. Cl.$^5$ .................. C12N 1/08; C12N 1/06; C12P 19/34
[52] U.S. Cl. .................. 435/270; 435/259; 435/820; 435/91; 536/23.1
[58] Field of Search .................. 435/270, 91, 820, 259; 536/27, 28, 29

[56] References Cited

U.S. PATENT DOCUMENTS

| | | | |
|---|---|---|---|
| Re. 25,785 | 6/1965 | Beers | 435/270 |
| 3,163,638 | 12/1964 | Miwa et al. | 435/270 |
| 3,582,468 | 6/1971 | Birnbaum et al. | 435/270 |
| 4,830,969 | 5/1989 | Holmes | 435/270 |
| 4,843,012 | 6/1989 | De Bonville et al. | 435/270 |
| 5,047,345 | 9/1991 | De Bonville et al. | 435/270 |

OTHER PUBLICATIONS

Jhingan, Anil K., Meth. Mol. Cell. Biol. (1992) 3:15–22 (accepted for publication) "A Novel Technology For DNA Isolation".
Kreike, J., Plant Mol. Bio. 14, 877–879 (1990) "Genetic Analysis of Forest Tree Populations: Isolation of DNA From Spruce and Fir Apices".
Kamalay, J. C., et al., Crop Science 30, 1079–1084 (1990) "Isolation and Analysis of Genomic DNA from Single Seeds".
P. G. Hempstead, et al., Dna and Cell Biology 9, 57–61 (1990) "Laboratory Methods, A Method for the Preparation of High-Molecular-Weight DNA from Marine and Freshwater Triclads (Platyhelminthes, Turbellaria)".
J. M. Henry, et al., Anal. Biochem. 185, 147–150 (1990) "Isolation of High-Molecular-Weight DNA from Insects".
J. A. Couch, et al., Plant Mol. Bio. Reporter 8, pp. 8–12 (1990) "Isolation of DNA from Plants High in Polyphenolics".
A. Kochko et al., Plant Mol. Bio. Repoter 8, pp. 3–7 (1990) "A Rapid and Efficient Method for the Isolation of Restrictable Table DNA from Plants of the Genus Abelmoschus".
H. Junghans, et al., Biotechniques 8, 176 (1990) "A Simple and Rapid Method for the Preparation of Total Plant DNA".
F. Guidet, et al., Nucleic Acids Res. 18, 4955 (1990) "A Rapid Method of Preparing Megabase Plant DNA".
J. L. Doyle, et al., Focus 12, pp. 13–15 (1990) "Isolation of Plant DNA from Fresh Tissue".
M. B. Johns, Jr., et al., Anal. Biochem. 190, pp. 276–278 (1989) "Purification of Human Genomic DNA from Whole blood Using Sodium Perchlorate in Place of Phenol".
I. J. Mettler, Plant Mol. Bio. Reporter 5, 346–349 (1987) "A Simple and Rapid Method for Minipreparation of DNA from Tissue Cultured Plant Cells".
J. J. Doyle, et al., Phytochemical Bull. 19, 11–15 (1987) "A Rapid DNA Isolation Procedure for Small Quantities of Fresh Leaf Tissue".
J. Hattori, et al., Anal. Biochem. 165, 70–74 (1987) "The Isolation of High-Molecular-Weight DNA from Plants".
S. O. Rogers, et al., Plant Mol. Bio. 5, 69–76 (1985) "Extraction of DNA from Milligram Amounts of Fresh, Herbarium and Mummified Plant Tissues".

(List continued on next page.)

*Primary Examiner*—Herbert J. Lilling
*Attorney, Agent, or Firm*—Nina L. Pearlmutter

[57] ABSTRACT

A novel method for the isolation of high molecular weight DNA from plants, yeast and bacteria using xanthate-forming compounds such as sodium/potassium ethyl xanthogenate is disclosed. The procedure does not require deproteination and yields clean DNA that is suitable for both PCR and Southern blotting. It can be utilized on a small scale without homogenizing the tissue. These features also facilitate automated screening of plant tissue samples, one of the labor-intensive techniques in molecular biology. This method is also adaptable for use in the field.

7 Claims, No Drawings

OTHER PUBLICATIONS

S. L. Dellaporta, et al., Maize Genetics Corp. Newsletter 57, 26–29 (1983) "Maize DNA Miniprep".

T. J. Close, et al., Gene 20, 305–316 (1982) "Construction and Characterization of the Chloramphenicol-Resistance Gene Cartridge: A New Approach to the Transcriptional Mapping of Extrachromosomal Elements".

E. A. Zimmer, et al., Maize for Biological Research, W. E. Sheridan, Ed. (University Press, Grand Forks, 1982) pp. 16–168 "A Simple Method for the Isolation of High Molecular Weight DNA from Individual Maize Seedlings and Tissues".

C. J. Rivin, et al., Maize for Biological Research, W. F. Sheridan, Ed. (University Press, Grand Forks, 1982), pp. 161–164 "Isolation of DNA and DNA Recombinants from Maize".

M. G. Murray et al., Nucleic Acids Res. 8, 4321–4325 (1980) "Rapid Isolation of High Molecular Weight Plant DNA".

N. Kislev, et al., Plant Physiol. 66, 1140–1143 (1980) "Utility of Ethidium Bromide in the Extraction from Whole Plants of High Molecular Weight Maize DNA".

F. B. Holl, Plant Tissue Culture Methods, O. L. Gamborg and L. R. Wetter, Eds. (National Research Council of Canada Saskatoon, 1975) pp. 65–69 "DNA Isolation from Plants for Use in DNA Feeding Experiments".

S. H. Howell, Mol. Tech. Approached Dev. Biol. 117 (1973) "The Isolation and Analysis of DNA from Eukaryotic Cells".

G. Guinn, Plant Physiol. 41, 689–695 (1966) "Extraction of Nucleic Acids from Lyophilized Plant Material".

J. W. Lyttleton, et al., Biochim, Biophys. Acta 80, 391–398 "The Isolation of Deoxyribonucleic Acid From Plant Tissues".

R. M. McCormick, Anal. Biochem. 181, 66–74 (1989) "A Solid-Phase Extraction Procedure for DNA Purification".

E. E. Reid, Organic Chemistry of Bivalent Sulphur, vol. 4 (Chemical Publishing Co., New York, 1962) pp. 131–195 "Thiocarbonic Acids and Derivatives".

E. M. Donaldson, Talanta 23, 417–426 (1976) "Solvent Extraction of Metal Xanthates".

DNA ISOLATION METHOD

TECHNICAL FIELD

This invention relates to the isolation of DNA from whole plants and plant cells, tissues and parts, and from yeasts and bacteria.

BACKGROUND OF THE INVENTION

With the increasing need for DNA fingerprinting, restriction fragment length polymorphism (RFLP) analysis, Southern transfers, construction of genomic libraries and transformation experiments in biotechnology, the isolation of high molecular weight (HMW) DNA becomes a major problem. Several procedures for the isolation of HMW DNA have been reported, all of which have drawbacks for various reasons. The methods generally involve physical grinding of cells or tissue followed by extraction in buffers containing detergent, EDTA, Tris and other reagents. Some of the reagents used react with various cellular organelles; the function of others is unknown. The prior art methods are often time consuming, irreproducible and give variable yields of DNA, involving more art than science. The DNA obtained also varies in terms of its purity, and all of the methods involve purification of DNA with phenol, a protein denaturant which can be hazardous to users. Finally, a method that is effective in DNA extraction in one plant group often fails when used on other plants.

More recently, a solid phase extraction material comprising silica and having hydroxyl groups on its surface has been reported as a replacement for phenol for removal of proteins. However, the preparation of this material is cumbersome, and grinding of tissue is still needed.

In view of these difficulties, a continuing need exists for a versatile method that would overcome these problems. It is an object of this invention to provide such a method.

DISCLOSURE OF THE INVENTION

While not intending to be limited by theory, the isolation of DNA from plants, yeasts and bacteria is difficult partly due to the presence of a rigid cell wall which is rich in polysaccharides and therefore difficult to rupture completely with commonly used buffers. Removal of the cell wall by enzymes is tedious and not always feasible. Variations in DNA yield and quality from extraction to extraction using current methods probably arises from the varying degrees of cell wall break up. Thus, there has been a need for new technique for disrupting cell walls by a thorough, yet delimited mechanism to allow isolation of DNA in a reproducible manner without the need to homogenize cells or tissues.

Polyhydric alcohols, including cellulose, have been solubilized in the past by conversion to metal xanthates. This method was discovered by Zeise in 1815 and it has been widely employed in the textile industry. Xanthates find extensive application in the separation and quantitative determination of numerous metal ions by taking advantage of the low and differential solubilities of metal xanthates under controlled pH conditions.

It has now been determined that the replacement of existing reagents for DNA extraction by xanthate-forming compounds is feasible and highly advantageous. It was postulated that these compounds would dissolve the cell wall in plants by forming water soluble polysaccharide xanthates with the hydroxyl groups of polysaccharides which make up a substantial portion of plant cell walls. The reaction of xanthate-forming compounds with amines is also reported. Furthermore, xanthate forming compounds can also bind metal ions to inhibit DNAase activity. As a result, these compounds enable selectively dissolving DNA from cell organelles, leaving contaminating proteins, metal ions and other compounds as an insoluble residue; DNA can then be precipitated from the supernatant.

Xanthate-forming compounds

The "xanthate-forming compounds" of this invention include any compound capable of forming xanthate reaction products with cell wall polysaccharides from plant cells. These specifically include carbon disulfide and its organoalkaline derivatives. While the common reagent used in industrial use of this reaction (the viscose rayon process) is carbon disulfide, for analytical isolation of DNA according to this invention the organoalkaline derivatives of carbon disulfide are preferred. By "organoalkaline derivatives of carbon disulfide" is meant compounds of the general formula

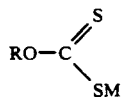

wherein R is an unsubstituted or substituted alkyl, alkenyl or aralkyl group, preferably selected from methyl, ethyl, propyl, butyl, hexyl, isoamyl, vinyl, allyl, 2-3-dihydroxypropyl, phenethyl, 4-morpholinylmethyl, and hydroxyphenethyl; and wherein M is an alkali metal or NH$_4$, preferably Na or K. These compounds are formed by reaction of carbon disulfide with the corresponding alcoholic alkali:

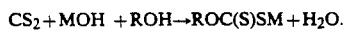

The most preferred of these compounds, the carbonodithioic acid o-ethyl ester, sodium salt (R=C$_2$H$_5$, M=Na; sodium ethyl xanthogenate) can be prepared by standard methods, and its potassium analogue is commercially available from Fluka. The entire class of compounds useful in this invention (including carbon disulfide) can thus be represented by the formula

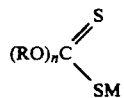

wherein is 0 or 1; R is an unsubstituted or substituted alkyl, alkenyl or aralkyl group, preferably selected from methyl, ethyl, propyl, butyl, hexyl, isoamyl, vinyl, allyl, 2-3-dihydroxypropyl, phenethyl, 4-morpholinylmethyl, and hydroxyphenethyl; and wherein M is alkali metal or ammonium, preferably Na or K, when n is 1 and another bond to the carbon when n is 0.

The methods described herein using these compounds enable efficient DNA isolation without homogenizing tissues and without removing proteins.

EXAMPLE I

Tissue Grinding Protocol

Fresh leaf material (0.6–0.63 g) of thirteen day old corn seedlings was frozen in a liquid nitrogen bath until it was very brittle and was ground to a fine powder using a glass homogenizer. The powder was suspended in 4 ml buffered extraction reagent (694 mM carbonodithioic acid, o-ethyl ester, sodium salt, 100 mM Tris, pH 7.5, 700 mM NaCl, 10 mM EDTA, pH 8 or 695 mM carbonodithioic acid, o-ethyl ester, potassium salt, 100 mM Tris, pH 7.5, 700 mM NaCl, 10 mM EDTA) in 15 ml propylene tube. After 5 min. incubation at 65°, the leaf debris was removed by filtering the homogenate through Miracloth. The DNA was precipitated from the filtrate by addition of two volumes of ethanol and centrifuged for 10 minutes at 3K at 4°. The pellet was suspended in 100 µl TE and centrifuged for 3 min. as before to remove precipitated proteins and metal xanthates. The supernatant was transferred into 1.5 ml Eppendorf tube and centrifuged for 5 minutes. The DNA was precipitated again from the supernatant by adjusting to 2M $NH_4OAC$ and adding two volumes of ethanol. DNA was pelleted by centrifuging for 5 min. at 735 g. After decanting the supernatant, the pellet was dried in a speed vac and redissolved in 100 µl TE buffer. The yield of DNA was 20–40 µg.

EXAMPLE II

Non-Grinding Protocol 1 g of fresh leaves in 4 ml of extraction buffer containing carbonodithioic acid, o-ethyl ester, sodium salt are incubated at 65° for 20 min. and filtered. The DNA is precipitated from the filtrate and reprecipitated as above. This non-grinding method applied to corn yielded 2.56 to 6.68 µg DNA per gram of leaf tissue.

EXAMPLE III

To evaluate the protocols of Examples I and II, DNA isolated was digested for 6 h with Bam HI and Hind III, EcoRI and Sst I and assayed by agarose gel electrophoresis. The undigested DNA showed an apparent molecular weight greater than the λ marker which is 23 kb. The absence of high molecular weight DNA and presence of smear in the digested samples suggested that DNA was completely digested and was free of contaminants which interfere with restriction enzyme digestion.

EXAMPLE IV

The quality of the DNA preparations was further assessed by Southern transfer experiments. Isolated DNA was digested with Bam HI, electrophoresed, transferred to MSI membrane and hybridized with 32 p single copy probes.

Undigested and digested DNA gave the expected hybridization pattern. The appearance of discrete bands in the digested samples confirmed that the DNA was digested completely by the enzyme and that the hybridization with the probe was successful. This is an important criterion for the quality of DNA.

EXAMPLE V

To further substantiate the quality of the isolated DNA for molecular biology applications, extracted DNA was assayed by polymerase chain reaction (PCR). After isolation, the DNA was amplified and the products were run on an agarose gel. A control experiment was also performed in which template DNA was not included in the PCR reaction. The absence of the expected target band in the control and its presence in the DNA samples obtained from the foregoing protocols further confirmed the quality of DNA.

EXAMPLE VI

The yield and efficiency of these extraction procedures was tested with a grinding protocol. Addition of a known amount (20 µg) of DNA to the leaf sample prior to homogenization and following the same steps yielded at least 81% DNA in the final step. This suggested that losses of DNA due to enzymatic or mechanical degradation were minimum.

EXAMPLES VII–XII

The grinding method has also been successfully employed for the isolation of DNA from thirteen day old seedlings of soybean, sorghum, sunflower, alfalfa and tobacco as determined by agarose gel electrophoresis and Southern transfers. Results are shown in Table 1.

TABLE 1

| Ex. | Plant | Yield[1] | High DNA Quality[2] | Southern Blot |
|---|---|---|---|---|
| VI | Alfalfa | 15–42 | Yes | works |
| VIII | Canola | 8–14 | Yes | |
| IX | Sorghum | 12–28 | Yes | works |
| X | Soybean | 26–37 | Yes | works |
| XI | Sunflower | 7–30 | Yes | |
| XII | Tobacco | 7–30 | Yes | |

[1] µg/600–630 mg fresh leaves
[2] DNA is completely digested by Bam HI

EXAMPLES XIII–XXIV

The versatility of these two methods (grinding and non-grinding) was also compared on alfalfa, barley, canola, sorghum, soybean, sunflower, tobacco, wheat, petunia, spinach, yeast and E. coli. With yeast and E. coli, homogenization was omitted in the grinding protocol. Table 2 gives the yields of DNA.

TABLE 2

| Ex. | Plant | Yield[1] grinding method | Yield[2] non-grinding method |
|---|---|---|---|
| XIII | Alfalfa | 15–42 | 1.50–2.80 |
| XIV | Canola | 8–14 | 2.70–4.80 |
| XV | Sorghum | 12–28 | 1.70–2.66 |
| XVI | Soybean | 26–37 | 0.45–1.14 |
| XVII | Sunflower | 7–30 | 0.13–1.34 |
| XVIII | Tobacco | 7–30 | 1.00–3.74 |
| XIX | Petunia | 11–19 | 2.07–2.27 |
| XX | Lettuce | 18–43 | 1.63–2.17[3] |
| XXI | Wheat | 7–38 | 1.12–4.27 |
| XXII | E. coli | 50 | 22–25 |
| Different Series: | | | |
| XXIII | Spinach | 20.64 | 1.4346 |
| XXIV | Yeast | 1.239 | 2.369 |

[1] µg/600–630 mg fresh tissue
[2] µg DNA/1 g fresh tissue
[3] µg DNA/2 g (market-purchased) lettuce

EXAMPLES XXV–XIX

The method of this invention was also applied successfully for the isolation of DNA from the following plants:

| Ex | Plant |
|---|---|
| XXV | Celosia |

| Ex | Plant |
|---|---|
| XXVI | Alyssum |

The simplicity of the non-grinding method may facilitate automation of DNA isolation and field use of analytical and diagnostic methods requiring DNA isolation by non-specialists. The wide applicability of the grinding method of this invention makes it a potential general method of DNA isolation from plant cells. The extractions have been attempted at various temperatures using different concentrations of substrates under various pH values, using different amounts and concentrations of buffer. With the non-grinding method, alfalfa, corn, sorghum and lettuce gave high yield and quality of DNA using 2 ml of buffer/reagent. On the other hand, isolation of DNA from soybean, sunflower and wheat using sodium ethyl xanthogenate required twice that amount to give clean DNA. With canola, tobacco and petunia, slight gentle homogenization prior to incubation helped to give better quality and yield of DNA. Thus, it can be seen that numerous specific embodiments of the methods of this invention can be optimized to suit the specific in vivo or in vitro system under consideration.

What is claimed is:

1. A method for disrupting cell walls in a DNA extraction process, comprising the steps of contacting the cells with an aqueous solution comprising a compound or compounds that form xanthate reaction products with cell wall polysaccharides and isolating DNA from the cells.

2. A method according to claim 1 wherein the compound or compounds has the formula

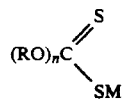

wherein n is 0 or 1; R is unsubstituted or substituted lower alkyl, lower alkenyl, or aralkyl; and M is alkali metal or ammonium when n is 1 and a sulfur-carbon bond when n is 0.

3. A method according to claim 2 wherein n is 1, R is unsubstituted or substituted lower alkyl, and M is Na or K.

4. A method according to claim 3 wherein R is selected from the group consisting of methyl, ethyl, propyl, butyl, hexyl, isoamyl, and 2-3-dihydroxypropyl.

5. A method according to claim 4 wherein the compound is the sodium or potassium salt of carbonodithioic acid o-ethyl ester.

6. A method according to claim 1, further comprising the step of filtering cellular debris from the solution.

7. A method according to claim 6, further comprising the step of precipitating the DNA from the filtered solution with ethanol.

* * * * *